United States Patent [19]
Garlich et al.

[11] Patent Number: 4,937,333
[45] Date of Patent: Jun. 26, 1990

[54] METHOD FOR PURIFYING AMINOMETHYLENEPHOSPHONIC ACIDS FOR PHARMACEUTICAL USE

[75] Inventors: Joseph R. Garlich, Lake Jackson; Jaime Simon, Angleton; Tipton T. Masterson, Lake Jackson, all of Tex.

[73] Assignee: The Dow Chemical Company, Midland, Mich.

[21] Appl. No.: 389,441

[22] Filed: Aug. 4, 1989

[51] Int. Cl.$^5$ ............................. C07F 9/38; C07F 9/66
[52] U.S. Cl. ...................................... 540/474; 562/14; 562/16
[58] Field of Search ...................... 540/474; 562/14, 16

[56] References Cited

U.S. PATENT DOCUMENTS

| | | | |
|---|---|---|---|
| 2,599,807 | 6/1952 | Bersworth | 562/14 |
| 3,288,846 | 11/1966 | Irani et al. | 562/16 |
| 3,738,937 | 6/1973 | Kautsky | 252/180 |

FOREIGN PATENT DOCUMENTS 55150501  5/1982  Japan.

OTHER PUBLICATIONS

Ixv. Akad. Nauk SSSR, Ser. Khim, 835, 1984.
Izv. Akad. Nauk SSSR, Ser. Khim, 844, 1984.
J. Magn. Reson. 76, 528 (1988).

Primary Examiner—David B. Springer

[57] ABSTRACT

High purity ethylenediaminetetra(methylenephosphonic acid) and 1,4,7,10-tetraazacyclododecane-1,4,7,10-tetra(methylenephosphonic acid) are prepared by dissolving the aminomethylenephosphonic acid in an aqueous base, acidifying with a mineral acid at an elevated temperature to precipitate the crystals, maintaining the solution at an elevated temperature for a period of time sufficient to assure crystallization, cooling to a lower temperature and maintaining at that temperature for a time sufficient to precipitate the crystals and filtering the resulting crystals at that temperature, washing the crystals with water and recovering the desired high purity aminophosphonic acid. The ethylenediaminetetra(methylenephosphonic acid) is obtained in a purer state during its synthesis if the crystals are filtered hot without prior cooling.

15 Claims, No Drawings

METHOD FOR PURIFYING AMINOMETHYLENEPHOSPHONIC ACIDS FOR PHARMACEUTICAL USE

BACKGROUND OF THE INVENTION

Organic aminophosphonic acids and their salts are well known as is their use in chelating metal ions, some of which are used as threshold inhibitors. U.S. Pat. No. 2,599,807 is an early patent which discloses these and describes methods for their preparation. An example of the preparation in this patent discloses heating an aqueous solution of ethylenediamine and adding to this a solution of the sodium salt of chloromethylenephosphonic acid and an excess of a base, e.g. $Na_2CO_3$ to maintain a pH of 10 to 11.5. After adding at least a stoichiometric amount of the phosphonating reagent, i.e. sufficient to form the completely phosphonated amine salt [sodium salt of ethylenediaminetetra(methylenephosphonic acid)], the solution is refluxed at its boiling point for from one to five hours. It is then cooled and neutralized to a pH of 6 to 7 and evaporated to dryness to recover the desired ethylenediaminetetra(methylenephosphonic acid).

Another method which makes the symmetrical ethylenediaminedi(methylenephosphonic acid) in good yield involves treating an aqueous solution of two molar portions of aminomethylenephosphonic acid with one molar portion of an alkylene dihalide at an elevated temperature for a time sufficient to insure complete reaction. This can be accomplished in a few hours under reflux in 50% ethanol.

In another patent, U.S. Pat. No. 3,738,987, the reaction to form the aminophosphonic acid is begun by introducing $PCl_3$ into water to form phosphorous acid and HCl. The polyamine is then introduced into this solution. It is preferred to have a 5 to 10% excess of the $PCl_3$. When the amine is added, the reaction medium is at a temperature of about 38° to 50° C. When all the amine has been added, the temperature is raised to 93° to 104° C. and an aqueous solution of formaldehyde is sparged into the reaction mixture, during which time the temperature is maintained at that level and for several hours thereafter and finally cooled.

In a more recent patent, Jap. No. 55-150501, it is disclosed that much higher yields are obtained by adding the amine to a mixture of phosphorous and hydrochloric acids in which the $H_3PO_3$ is in excess with respect to the amine, preferably about 4.3 to 5.5 moles of the acid per mole of amine. Concentrated HCl is used, preferably about 2.2 moles HCl per mole of amine. Too much acid will tend to increase the amount of water in the system which is undesirable. No additional water is added to the reaction mixture, which is apparently the reason for the improved yields since all the other methods use water and dilute acids.

It has recently been discovered that certain of the methylenephosphonated amines are useful for imaging and other radiopharmaceutical uses when complexed as chelates with radioactive metals. Use for such purposes requires the highest purity materials.

The present inventors have found that, even when using the preferred methods of the known art, impurities are formed, e.g. the N-methylated species in which an amine hydrogen is replaced by a methyl group rather than by the methylenephosphonic acid moiety.

SUMMARY OF THE INVENTION

Certain polyaminomethylenephosphonic acids, having sufficiently high purity for radiopharmaceutical use, have been prepared by recrystallizing by the steps of (1) dissolving in a base, e.g. $NH_4OH$, (2) acidifying with a mineral acid, e.g. HCl, to reprecipitate the phosphonic acid, (3) heating at reflux temperature for a period of time, (4) heating at a lower temperature, (5) filtering at the lower temperature, (6) washing the resulting crystals. The above steps are repeated as many times as necessary to obtain the desired purity. Products having 0.1% impurities or less are attainable by the method.

DETAILED DESCRIPTION OF THE INVENTION

The process of this invention is a method of crystallization which produces certain very high purity (99+%) aminomethylenephosphonic acids, e.g. ethylenediaminetetra(methylenephosphonic acid), EDTMP, and 1,4,7, 10-tetraazacyclododecane-1,4,7,10-tetra(methylenephosphonic acid), DOTMP. Other aminophosphonic acids are not easily purified in this manner because of their greater solubility in water at low pH values. For example, diethylenetriaminepenta(methylenephosphonic acid) [DTPMP] and nitrilotri(methylenephosphonic acid) [NTMP] cannot be purified by this process.

While a process to obtain high purity aminophosphonic acids is known, a process to make even higher purity such products is the subject of this invention. The present process involves certain procedures for recrystallization to obtain the desired high purity products.

The present process of recrystallization is accomplished by first dissolving the aminophosphonic acid in an aqueous base, preferably ammonium hydroxide, which is followed by acidifying the solution with a mineral acid to a pH within the range of from about 0 to about 4. The acidic solution is then refluxed for a period of time of from about one-half to about three hours, preferably from about one-half to about one hour. The solution is then cooled to a lower temperature of from about ambient to about 95° C., preferably from about 25° to about 45° C. and allowed to remain at that temperature for a period of time of from about one to about 24 hours, preferably from about 12 to about 24 hours. The precipitated, i.e. recrystallized, aminophosphonic acid is then filtered at the lower temperature to obtain the desired purified crystals which are then washed thoroughly with water to remove any solution which might contain undesired impurities. The process is repeated one or more times if the desired purity has not been attained. A product containing 0.1% or less impurities can be obtained by the above process.

Of course, the number of times the recrystallization process of this invention is repeated will depend on the purity desired in the final product and also on the purity of the starting aminomethylenephosphonic acid. The present inventors have determined that, in the case of ethylenediaminetetra(methylenephosphonic acid), if the reaction medium is filtered prior to substantial cooling, the resulting EDTMP product has a higher purity than if the reaction medium is cooled before filtering. Best results are obtained if the filtration is done while the reaction medium is at reflux temperature. It is believed that this is because the impurities are more soluble in the hot solution. The following example illustrates the method of preparation which results in the purest EDTMP product. Additional examples show the recrystallization process to provide the products which can be used for pharmaceutical purposes.

EXAMPLE 1

Preferred Preparation of EDTMP

A 5-L 3-neck flask equipped with a mechanical stirrer fitted with a Teflon paddle is charged with phosphorous acid (755 g) to which is added conc. HCl (1.2 L). After vigorous stirring, the phosphorous acid dissolves, causing the solution temperature to drop to 0° C. To this cold solution ethylenediaminedihydrochloride (271 g) is added and heat is applied with vigorous stirring. At about 60° C., a large volume of HCl gas is given off, which is conveniently recovered with a water gas trap. At about 88° C. all the ethylenediaminedihydrochloride is dissolved and heating is continued to 100° C. (reflux). Once the reaction has reached 100° C., a 37% aqueous solution of formaldehyde (902 mL) is added dropwise via a peristaltic pump over a 22-24 hour period (rate is 0.65 mL/min). After an additional four hour reflux time, the boiling suspension is vacuum filtered (1.5 L sintered glass filter) and washed with two 300 mL portions of water. This solid is air dried and 607 g (70% yield) of EDTMP, m.p. 216-217 d (lit. m.p. 214 d) is recovered. H-1 and P-31 NMR analyses of this sample indicate the impurities are at a level of less than 1%.

EXAMPLE 2

Purification of EDTMP

A quantity of 1050 g of the EDTMP prepared by the procedure of Example 1 was added to 1050 mL water in a 2-L round-bottomed flask and stirred with a mechanical stirrer fitted with a Teflon paddle. Concentrated NH$_4$OH (325 mL) was added in 25-mL increments over a one hour period. After all the NH$_4$OH was added, almost all the EDTMP had gone into solution. The small amount that was not soluble was removed by vacuum filtration. The clear filtrate was then poured with stirring into 2100 mL of refluxing 3M hydrochloric acid in a 5-L round-bottomed flask equipped with a heating mantle and thermometer (set at 100° C.). The resulting stirred solution was clear and the temperature had dropped to 68° C. Stirring was continued and after six minutes the temperature had risen to 72° C. and a slight precipitate was visible. Within 16 minutes, with continued stirring, the temperature was 87° C. and the precipitate was heavy. After 20 minutes, the temperature was again at reflux (100° C.). After 30 minutes at reflux temperature, the thermometer setting was lowered to 43° C. After stirring for 21 hours at 43° C., the suspension was vacuum filtered through a sintered glass funnel while still warm. Water (500 mL) was used to transfer the heavy solid from the flask to the filter funnel. The filter cake thus obtained was washed with three 500-mL portions of water and air dried overnight to give 984.8 g of EDTMP, m.p. 214°-215° C. A P-31 NMR spectrum of this sample indicated ca. 0.6% impurity. The EDTMP used as starting material had impurity levels of about 1%.

EXAMPLE 3

Purification of EDTMP

A sample of EDTMP prepared in Example 2 (970 g, 0.6% impurity) was dissolved in 970 mL of water in a 2-L round-bottomed flask by the addition of 323 mL of concentrated NH$_4$OH in 25-mL portions. After all solids were dissolved, the solution was poured with stirring into 1940 mL of refluxing 3N aqueous HCl. The temperature dropped to 74° C. and after seven minutes, had risen to 82° C. with a faint precipitate visible. After 30 minutes, more precipitate had formed and the temperature had reached 100° C. The suspension was left at reflux for an additional hour after which the temperature was lowered to 43° C. and stirred for an additional 13 hours. At the end of this time, the suspension was vacuum filtered using 450 mL of water to transfer, washed with three 400-mL portions of water and air dried to give 920.4 g of EDTMP, m.p. 214°-215° C. A P-31 NMR spectrum of this sample indicated ca. 0.4% impurity level.

The following Examples illustrate the purification of EDTMP from different sources.

EXAMPLE 4

Purification of EDTMP

The product of Example 3 (0.4% impurity, 900 g) was dissolved in 900 mL of water in a 2-L round-bottomed flask by the addition of 300 mL conc. NH$_4$OH over a 20-minute period. The solution was poured with stirring into 1800 mL of refluxing 3N aqueous HCl. The temperature of the resulting solution dropped to 72° C. and after five minutes of stirring with heat it had risen to 78° C. with some precipitate present. Within 30 minutes the temperature was back to 100° C. and was left there for one hour after which the temperature was lowered to 43° C. After stirring overnight (17.5 hours) at 43° C., the heavy precipitate was vacuum filtered using 400 mL of water to transfer, washed with three 400-mL portions of water and air dried to give 805.62 g of EDTMP, m.p. 215°-217° C. A high field P-31 NMR spectrum indicated an impurity level of around 0.1% for this sample of EDTMP.

EXAMPLE 5

Purification of EDTMP

A sample (50 g, 115 mmoles) of EDTMP containing 5.81% impurities by P-31 NMR was dissolved in 50 mL of water by the addition of 13.5 mL (193 mmoles) conc. NH$_4$OH in small portions over a period of 15 minutes. This solution of the ammonium salt of EDTMP was then poured with stirring into 100 mL (300 mmoles) of refluxing 3N HCl. The temperature, which dropped to 73° C., was brought back to reflux (100° C.) with application of additional heat and vigorous stirring. The EDTMP began precipitating from solution almost immediately and continued to precipitate with continued stirring and heating. The solution was maintained at reflux for one hour after which the temperature was lowered to 43° C. and the suspension allowed to stir for 21 hours after which the heavy white precipitate was vacuum filtered at that temperature, using 25 mL of water to transfer and three additional 25 ML portions of water to wash the precipitate. The precipitate was air dried to give 44.2 g (101 mmoles, 89% yield) of EDTMP. Analysis of this precipitate by P-31 NMR indicated the impurity level had dropped to 2.38%.

EXAMPLE 6

Purification of EDTMP

A sample (50 g, 115 mmoles) of EDTMP containing 5.81% impurities by P-31 NMR was dissolved in 50 mL of water by the addition of 13 mL (186 mmoles) conc.

NH₄OH in small portions over a period of 15 minutes. This solution of the ammonium salt of EDTMP was then poured with stirring into 100 mL (300 mmoles) of refluxing 3N HCl. The temperature, which dropped to 72° C., was brought back to reflux (100° C.) with application of additional heat and vigorous stirring. The EDTMP began precipitating from solution almost immediately and continued to precipitate with continued stirring and heating. The solution was maintained at reflux with stirring for 22 hours after which the heavy white precipitate was vacuum filtered at that temperature, using 25 mL of water to transfer and three additional 25 mL portions of water to wash the precipitate. The precipitate was air dried to give 34.3 g (79 mmoles, 69% yield) of EDTMP. Analysis of this precipitate by P-31 NMR indicated the impurity level had dropped to 1.45%.

EXAMPLE 7

Purification of EDTMP

A sample (50 g, 115 mmoles) of EDTMP containing 5.81% impurities by P-31 NMR was dissolved in 50mL of water by the addition of 13 mL (186 mmoles) conc. NH₄OH in small portions over a period of 15 minutes. This solution of the ammonium salt of EDTMP was then poured with stirring into 100 mL (300 mmoles) of refluxing 3N HCl. The temperature, which dropped to 72° C., was brought back to reflux (100° C.) with application of additional heat and vigorous stirring. The EDTMP began precipitating from solution almost immediately and continued to precipitate with continued stirring and heating. The solution was maintained at reflux for one hour after which the temperature was lowered to 70° C. and the suspension allowed to stir for 21 hours after which the heavy white precipitate was vacuum filtered at that temperature, using 25 mL of water to transfer and three additional 25 mL portions of water to wash the precipitate. The precipitate was air dried to give 41.4 g (95 mmole, 83% yield) of EDTMP. Analysis of this precipitate by P-31 NMR indicated the impurity level had dropped to 2.05%.

EXAMPLE 8

Purification of EDTMP

A sample (50 g, 115 mmoles) of EDTMP containing 5.81% impurities by P-31 NMR was dissolved in 50 mL of water by the addition of 13 mL (186 mmoles) conc. NH₄OH in small portions over a period of 15 minutes. This solution of the ammonium salt of EDTMP was then poured with stirring into 100 mL (300 mmoles) of refluxing 3N HCl. The temperature, which dropped to 72° C., was brought back to reflux (100° C.) with application of additional heat and vigorous stirring. The EDTMP began precipitating from solution almost immediately and continued to precipitate with continued stirring and heating. The solution was maintained at reflux for one hour after which the heat source was removed and the suspension allowed to stir at room temperature for 21 hours after which the heavy white precipitate was vacuum filtered at that temperature, using 25 mL of water to transfer and three additional 25 mL portions of water to wash the precipitate. The precipitate was air dried to give 41.2 g (94 mmole, 82% yield) of EDTMP. Analysis of this precipitate by P-31 NMR indicated the impurity level had dropped to 2.11%.

EXAMPLE 9

Purification of EDTMP

A sample (50 g, 115 mmole) of EDTMP (DEQUEST 2041, a commercial sample) containing 3.65% impurities by P-31 NMR was dissolved in 50 mL of water by the addition of 16 mL (229 mmoles) conc. NH₄OH in small portions over a period of 15 minutes. This solution of the ammonium salt of EDTMP was then poured with stirring into 100 mL (300 mmoles) of refluxing 3N HCl. The temperature, which dropped to 72° C., was brought back to reflux (100° C.) with application of additional heat and vigorous stirring. The EDTMP began precipitating from solution almost immediately and continued to precipitate with continued stirring and heating. The solution was maintained at reflux for one hour after which the temperature was lowered to 43° C. and the suspension allowed to stir for 21 hours after which the heavy white precipitate was vacuum filtered at that temperature, using 25 mL of water to transfer and three additional 25 ML portions of water to wash the precipitate. The precipitate was air dried to give 44.3 g (102 mmole, 89% yield) of EDTMP. Analysis of this precipitate by P-31 NMR indicated the impurity level had dropped to 1.85%.

A trademark of the Monsanto Company for a series of aminophosphonic acid chelating agents.

EXAMPLE 10

Purification of EDTMP

A sample (50 g, 115 mmoles) of EDTMP containing 5.81% impurities by P-31 NMR was dissolved in 50 mL of water by the addition of 16 mL (229 mmoles) conc. NH₄OH in small portions over a period of 15 minutes. This solution of the ammonium salt of EDTMP was then poured with stirring into 100 mL (300 mmoles) of refluxing 3N HCl. The temperature, which dropped to 72° C., was allowed to cool to 43° C. with continued vigorous stirring. The EDTMP began precipitating from solution almost immediately and continued to precipitate while the suspension was allowed to stir for 21 hours at 43° C. The heavy white precipitate was then vacuum filtered at that temperature, using 25 mL of water to transfer and three additional 25 mL portions of water to wash the precipitate. The precipitate was air dried to give 42.7 g (98 mmole, 85% yield) of EDTMP. Analysis of this precipitate by P-31 NMR indicated the impurity level had dropped to 2.95%.

Examples A and B following are comparative.

EXAMPLE A

A 5 g (8.73 mmoles) sample of diethylenetriaminepenta(methylenephosphonic acid), DTPMP, was dissolved in 4 mL of water by the addition of 1.526 mL (21.82 mmoles) conc. NH₄OH in small portions over a period of 15 minutes. This solution of the ammonium salt of DTPMP was then poured with stirring into 9.15 mL (27.45 mmoles) of refluxing 3N HCl. The temperature, which dropped to 76° C., was brought back to reflux (100° C.) with application of additional heat and vigorous stirring. The solution was maintained at reflux for one hour after which the temperature was lowered to 43° C. and the suspension allowed to stir for 91 hours. Even at the end of this lengthy period of stirring, no precipitate had formed. The solution was allowed to remain at room temperature without stirring for an additional 8 days with periodic observation. No precipitate had formed at the end of this time.

EXAMPLE B

A sample of nitrilotri(methylenephosphonic acid), NTMP, (3 g, 10 mmoles) was dissolved in 4.32 mL of water by the addition of 1.049 mL (15.0 mmoles) conc. NH4OH in small portions over a period of 15 minutes. This solution of the ammonium salt of NTMP was then poured with stirring into 6.3 mL (18.9 mmoles) of refluxing 3N HCl. The temperature, which dropped to 83° C., was brought back to reflux (100° C.) with application of additional heat and vigorous stirring. The solution was maintained at reflux for one hour after which the temperature was lowered to 43° C. and allowed to stir at that temperature for 89 hours. Even at the end of this lengthy period of stirring, no precipitate had formed. The solution was allowed to remain at room temperature without stirring for an additional 8 days with periodic observation. No precipitate had formed at the end of this time.

EXAMPLE 11

Preparation of DOTMP

Into a 100 mL, three-necked, round-bottomed flask, equipped with a thermometer, reflux condenser and heating mantle, was placed 3.48 g (20.2 mmoles) of 1,4,7,10-tetraazacyclododecane (a commercial product obtained from Parish Chemical Company, Orem, Utah) and 14 mL water. To this solution was added 17.2 mL of conc. HCl and 7.2 g of H3PO3 (87.7 mmoles) and the solution was heated to 105° C. The refluxing solution was stirred vigorously while 13 g (160.2 mmoles) of formaldehyde (37% aq. soln.) was added over a period of one hour. The refluxing solution was stirred an additional two hours. The heat was then removed and the solution allowed to cool to room temperature and stand for 62.5 hours. The reaction solution was concentrated by heating at 40° C. in vacuo to a reddish brown semi-solid. A 30-mL portion of water was added which produced a suspension. This suspension was then poured into 400 mL of acetone with vigorous stirring. The resulting off-white precipitate was vacuum filtered and dried overnight to give 10.69 g (97% yield) of DOTMP.

EXAMPLE 12

Purification of DOTMP

A 2.0 g (3.65 mmoles) sample of DOTMP from Example 11 was dissolved in 2 mL of water by the addition of 700 μL conc. NH4OH in 100 μL portions to give a solution having a pH of 2-3. This solution was then added all at once to 4.5 mL of 3N HCl (13.5 mmoles), mixed well, and allowed to stand. Within one hour, small nearly square crystals had begun to form on the sides of the glass below the surface of the liquid. The crystal growth was allowed to continue and the crystals were gently bumped off the vessel walls, filtered, washed with four 3-mL portions of water and air dried to constant weight to give 1.19 g (60% yield) of white crystalline solid m.p. 270 (d)°C.

The DOTMP signal in the decoupled P-31 NMR spectrum of the starting material represented 78.1% of the total phosphorous signals present while that of the product obtained after the base/acid recrystallization, represented 94.7% of the total phosphorous present.

EXAMPLE 13

Preparation of DOTMP

Into a 250-mL three-necked, round-bottomed flask, fitted with a thermometer, temperature controller, addition funnel and stirring bar and attached to a reflux condenser was placed 6.96 g (0.04 mole) 1,4,7,10-tetraazacyclododecane (a commercial product obtained from Parish Chemical Company, Orem, Utah). To this was added 14.5 g (1.77 moles) phosphorous acid, 30 mL deionized water and 28 mL (0.336 mole) conc. HCl. After the solution had been brought to reflux temperature (105° C.), aqueous (37%) formaldehyde (26.0 g, 0.32 mole) was introduced into the flask through the addition funnel during a 30 to 40-minute period. The solution was heated and stirred for three more hours at reflux and then permitted to cool to ambient temperature.

The reaction solution was then transferred to a 500 mL round bottomed flask an attached to a rotoevaporator apparatus. The solution was evaporated to an amber, viscous semi-solid, the temperature never exceeding 40° C. in the heating bath. To the viscous material was added cc. 300 mL HPLC grade acetone, producing a light brown, sticky, viscous oil which was then dissolved in 22 mL of water and added slowly with vigorous stirring to 1 L of acetone. The acetone was decanted and the light colored oil dried under vacuum to give 16.6 g (76% yield) of crude DOTMP. A portion (13.1 g) of the crude DOTMP was dissolved in 39.3 g deionized water, treated with a seed crystal and allowed to stand overnight. The resulting precipitate was vacuum filtered, washed with cold water and dried under vacuum to give 4.75 g (36% yield) of DOTMP.

EXAMPLE 14

Purification of DOTMP

A quantity (3.0 g, 5.47 mmoles) of the DOTMP prepared in Example 13 was recrystallized by dissolving it in 3 mL of water by the addition of 2.2 mL (31.5 mmoles) of conc. NH4OH. This solution was added with stirring to 2.4 mL (28.8 mmoles) of conc. HCl at which time a white solid precipitated. This precipitate was vacuum filtered and dried to give 2.42 g (81% yield) of DOTMP, m.p. 280 (d)°C.

The DOTMP signal in the decoupled P-31 NMR spectrum of the starting material represented 97.2% of the total phosphorous signals present. The DOTMP signal in the decoupled 31-P NMR spectrum of the product after the base/acid recrystallization, represented 98.2% of the total phosphorous signals present.

EXAMPLE 15

Purification of DOTMP

Into a 250-mL beaker containing 85.77 g (0.871 mole) conc. HCl was added (57.11 g, 0.696 mole) solid phosphorous acid and dissolved with stirring. A 250 mL three-necked, round-bottomed flask was loaded with 1,4,7,10-tetraazacyclododecane (10.00 g, 0.58 mole) and attached to a reflux condenser. This apparatus was placed on a heater/stirrer and fitted with a thermometer which controlled an infra-red lamp through a temperature controller. The acid solution was carefully added to the reaction flask containing 1,4,7,10-tetraazacyclododecane The reaction mix, which had become a white slurry, was brought to reflux temperature (ca. 105° C.). Aqueous 37% formaldehyde solution (94.12 g, 1.16 moles) was added all at once to the reaction mix. The slurry immediately turned to a clear solution. The reaction was continued at reflux with constant stirring for approximately five hours. The reaction solution was cooled and 188 mL transferred to a one liter Erlenmeyer flask and diluted with 470 mL of 0.1 M hydrochloric acid solution (1 to 3.5 dilution). The solution was seeded with a few grains of DOTMP and placed in the refrigerator overnight. The resulting white solid precipitate (1.35 g) was collected 17 hours later by filtration on a medium glass fritted funnel. The filtrate was transferred from the filter flask back into the one liter Erlenmeyer, seeded again with a few grains of DOTMP, and placed in the refrigerator overnight. The next day the white precipitate was filtered (2.70 g) and the filtrate concentrated under vacuum to 80 mL. This filtrate was then diluted with 200 mL of water, seeded as above and allowed to stand in a refrigerator for 72 hours, after which the white solid was filtered and dried to give 8.85 g (28% yield) of DOTMP.

EXAMPLE 16

Purification of DOTMP

In the reactor of Example 15 a 50 mL three-necked flask was loaded with 15.6 mL of 3N HCl solution (46.8 mmoles) and placed on a heater/stirrer. This solution was taken up to reflux temperature (ca. 103° C.) A separate solution was made by placing DOTMP (8.00 g, 14.6 mmoles), prepared in Example 15, into a 50 mL beaker and dissolving it by adding 8.00 g HPLC grade water and (2.52 mL, 36.0 mmoles) of concentrated (14.3M) ammonium hydroxide.

The DOTMP/NH$_3$ solution was added all at once with constant stirring to the refluxing 3N HCl solution. The temperature dropped to ca.75° C. and was quickly brought back to reflux and maintained there for about one hour. The temperature was lowered to 43° C. and maintained there for a period of 21 hours. This slurry was then filtered through a glass medium filter funnel, transferring it with ca. 4 mL water and washing the filter cake additionally with ca. 4 mL of water. The filter cake was air dried to give 6.79 g (85% yield) of a fine, white solid. Analysis showed that the coproducts were reduced from 6.85% in the original DOTMP sample of Example 15 to 3.11% in this sample.

EXAMPLE 17

Purification of DOTMP

Into a 50-mL three-necked flask, fitted with a thermometer and water jacketed condenser, was introduced a 3N HCl solution (13.25 mL, 39.76 mmoles). This apparatus was placed on a heater/stirrer and heated to reflux.

A separate solution of DOTMP was prepared by adding the DOTMP (6.79 g, 12.38 mmoles), prepared in Example 12, to a 50 mL beaker and dissolving it by adding 6.8 g of water and 2.14 mL (30.59 mmoles) of concentrated ammonium hydroxide. This solution was filtered through a paper filter to remove trace solids; then added all at once to the refluxing hydrochloric acid solution prepared above. The resulting white suspension was heated for one hour at reflux and then the temperature was lowered to 43° C. After allowing the suspension to stir at this temperature for a total of ca. 21 hours the white solid was filtered through a fine glass fritted funnel, washed with cn. 8 mL of deionized water, then allowed to air dry. A total of 6.14 g (90% yield) of DOTMP was thus recovered as a fine white solid. Analysis by P-31 NMR showed an increase in purity from 96.89% for the DOTMP used as starting material to 98.37% for the DOTMP product recovered.

EXAMPLE 18

Purification of DOTMP

A 50 mL three-necked, round bottomed flask was loaded with 12.0 g (36.0 mmoles) of 3N hydrochloric acid solution. A stir bar was added and the HCl solution was brought up to reflux temperature with constant stirring.

A 50 mL beaker was loaded with 6.14 g (11.2 mmoles) of DOTMP prepared in Example 17. An equal weight of deionized water was added (341.1 mmoles) and the DOTMP was brought into solution through the addition of 1.94 mL (27.7 mmoles) of concentrated ammonium hydroxide. This solution was filtered through a paper filter to remove undissolved solids, then added all at once with vigorous stirring to the refluxing hydrochloric acid solution. A white precipitate formed immediately from the addition of the two water-clear solutions. The suspension was heated to reflux and allowed to stir for about one (1) hour at this temperature. The temperature of the flask was then lowered to ca. 43° C. and allowed to stir at this temperature for a total of about 21 hours.

The white solid was filtered at this temperature, washed with 8 mL of water and air dried to give 5.90 g (87% yield) of purified DOTMP. Analysis by P-31 NMR indicated greater that 99% purity of DOTMP had been achieved.

EXAMPLE 19

Purification of DOTMP

The 1.35 g sample and the 2.7 sample of DOTMP prepared in Example 15 were combined and ground to a fine powder. A P-31 NMR analysis of this sample indicated 6.40% non-DOTMP phosphorous-containing by-products were present. A 1.00 g (1.82 mmoles) sample of this DOTMP was added to a 3-dram vial along with a 1.00 g portion of water and a stir bar. This slurry was stirred while adding concentrated ammonium hydroxide (315 μL, 4.5 mmoles) in small portions (42 μL) until completely dissolved.

A 4-dram vial was loaded with 1.95 mL of 3N HCl solution (5.85 mmoles) and equipped with a stirring bar and reflex condenser. This solution was brought to reflux temperature using a mineral oil bath. The DOTMP solution from above was added to the refluxing HCl solution with stirring dropping the temperature to 75° C. This solution was again brought to reflux and held for one hour with constant stirring. The temperature was then lowered to 43° C. and held there with constant stirring for a total of 21 hours. The white precipitate was then filtered and washed with 4 portions of 0.5 mL of cold water. The 0.72 g (72% yield) of DOTMP thus purified showed only 2.28% phosphorous containing by-products when analyzed by P-31 NMR.

EXAMPLE 20

Purification of DOTMP

The recrystallization of Example 19 was repeated except that after the one hour reflux period the solid was filtered while hot, washed with hot water, and dried to give 0.84 g (84% yield) of DOTMP. This material was analyzed by P-31 NMR and found to contain only 1.74% phosphorous containing by-products as compared to 6.40% present in the starting DOTMP.

EXAMPLE C (COMPARATIVE)

In the apparatus of Example 13 was placed 7.51 g (0.125 mole) ethylenediamine, 47.3 g (0.5 mole) phosphorous acid, 59 mL conc. HCl (0.737 mole) and 80 mL water. The solution was heated to reflux with stirring and treated with 16.6 g (0.5 mole) paraformaldehyde, added in small portions over a one hour period. The solution was then refluxed an additional 2.5 hours and allowed to cool to room temperature overnight. The resulting white solid EDTMP was then vacuum filtered and washed with two 50-mL portions of water. This procedure gave 32.27 g (60% yield) EDTMP. Analysis of this sample by P-31 NMR indicated a 6.4% level of by-products present.

EXAMPLE 21

The procedure of Comparative Example C above was repeated using half the above amounts. After all the paraformaldehyde had been added, a portion of the reaction solution was maintained at 90°-97° C. overnight after which a voluminous white precipitate had appeared. The suspension was filtered while still hot and washed with two 40-mL portions of hot 3N HCl. The solid thus isolated was air-dried to give 5.25 g EDTMP, containing only 1.4% by-product level.

We claim:

1. A process for purifying ethylenediaminetetra(methylenephosphonic acid) and 1,4,7,10-tetraazacyclodo-decane-1,4,7,10-tetra(methylenephosphonic acid) which comprises the steps of: (a) dissolving the aminophosphonic acid in an aqueous base, (b) adding the solution from step (a) to an acid solution maintained at an elevated temperature to reprecipitate the aminophosphonic acid, (c) heating the solution at an elevated temperature for a period of time sufficient to assure that precipitation of the aminophosphonic acid has begun, (d) cooling the solution to a lower temperature and allowing it to remain at that temperature for a period of time sufficient to assure precipitation of the aminophosphonic acid, (e) filtering the aminophosphonic acid crystals at the lower temperature and finally (f) washing the crystals with water.

2. The process of claim 1 wherein the aqueous base is ammonium hydroxide.

3. The process of claim 2 wherein the acid solution in step (b) is a solution of a mineral acid.

4. The process of claim 3 wherein the mineral acid is hydrochloric acid.

5. The process of claim 4 wherein the temperature in step (d) is in the range of from about ambient to about 95° C.

6. The process of claim 1 wherein for the purification of ethylenediaminetetra(methylenephosphonic acid) step (d) is omitted.

7. The process of claim 1 wherein the heating period in step (c) is from about one-half to about three hours.

8. The process of claim 7 wherein the heating period in step (c) is from about one-half to about one hour.

9. The process of claim 7 wherein the time period in step (d) is from about one to about 24 hours.

10. The process of claim 9 wherein the time period in step (d) is from about 12 to about 24 hours.

11. The process of claim 1 wherein the temperature of step (c) is 35°-105° C.

12. The process of claim 11 wherein the temperature is 70°-105° C.

13. The process of claim 1 wherein steps a through f, inclusive, are repeated at least once.

14. In the process for preparing ethylenediaminetetra(methylenephosphonic acid) by reacting ethylenediamine, phosphorous acid, hydrochloric acid and formaldehyde or paraformaldehyde and heating the reaction medium to reflux temperature, the improvement which comprises filtering the product from the reaction medium prior to cooling.

15. The process of claim 14 wherein the filtration is accomplished while the reaction medium is at reflux temperature.

16. The process of claim 14 wherein the ethylenediamine is in the form of the hydrochloride.

* * * * *

UNITED STATES PATENT AND TRADEMARK OFFICE
CERTIFICATE OF CORRECTION

PATENT NO. : 4,937,333

DATED : June 26, 1990

INVENTOR(S) : Joseph R. Garlich, Lake Jackson; Jaime Simon, Angleton; Tipton T. Masterson, Lake Jackson, all of Texas.

It is certified that error appears in the above-identified patent and that said Letters Patent is hereby corrected as shown below:

Col. 6, Line 4, "A sample (50 g, 115 mmole) of EDTMP (DEQUEST" Should correctly read -- A sample (50 g, 115 mmole) of EDTMP (DEQUEST* --

Col. 8, Line 25, "material was added cc. 300 mL HPLC grade acetone," Should correctly read -- material was added ca. 300 mL HPLC grade acetone, --

Col. 10, Line 1, "fritted funnel, washed with cn. 8 mL of deionized wa-" Should correctly read -- fritted funnel, washed with ca. 8 mL of deionized wa- --

Signed and Sealed this

Tenth Day of December, 1991

Attest:

HARRY F. MANBECK, JR.

*Attesting Officer*     *Commissioner of Patents and Trademarks*